United States Patent [19]

Arnold

[11] Patent Number: 4,587,252

[45] Date of Patent: May 6, 1986

[54] HYDROCODONE/IBUPROFEN PHARMACEUTICAL COMPOSITIONS AND METHOD

[75] Inventor: John D. Arnold, Kansas City, Mo.

[73] Assignee: Brighton Pharmaceutical, Inc., Kansas City, Mo.

[21] Appl. No.: 682,906

[22] Filed: Dec. 18, 1984

[51] Int. Cl.[4] .................... A61K 31/19; A61K 31/44; A61K 31/185

[52] U.S. Cl. ................................ 514/282; 514/570; 514/576

[58] Field of Search ............... 424/260, 317; 514/282, 514/570, 576

[56] References Cited

PUBLICATIONS

S. A. Cooper et al., "Relative Efficacy of an Ibuprofen-Codeine Combination", Clin. Pharmacol. Ther., 27 (2) (1980), p. 249.

*Primary Examiner*—Stanley J. Friedman
*Attorney, Agent, or Firm*—Hedman, Gibson, Costigan & Hoare

[57] ABSTRACT

Pharmaceutical compositions containing hydrocodone or a pharmaceutically acceptable acid addition salt thereof and ibuprofen or a pharmaceutically acceptable salt thereof are useful in treating pain in mammals.

6 Claims, No Drawings

HYDROCODONE/IBUPROFEN PHARMACEUTICAL COMPOSITIONS AND METHOD

FIELD OF THE INVENTION

This invention relates to pharmaceutical compositions possessing analgesic activity.

BACKGROUND OF THE INVENTION

Hydrocodone (7,8-dihydrocodienone) is a centrally acting narcotic analgesic agent with actions qualitatively similar to those of codeine. The compound is 4,5-alpha-epoxy-3-methoxy-17-methylmorphinan-6-one. The preparation of hydrocodone and its pharmaceutically acceptable acid addition salts are described in, for example, Pfister and Tischler, U.S. Pat. No. 2,715,626, Merck Index, (Ninth Edition) Entry No. 4672 (1976). Ibuprofen is an antiinflammatory agent and has also been recommended for the relief of pain in man and animals. The compound is 2-(4-isobutylphenyl)propionic acid and it is described, together with its pharmaceutically acceptable salts, in, for example, U.K. Patent Specification No. 971,700.

This invention provides a combination of these two agents. The combination provides an analgesic effect greater than that obtained by increasing the dose of either constituent administered alone. The adverse effects produced by such combination are considered to be less than those produced by an equi-analgesic dose of one of the constituents.

SUMMARY OF THE INVENTION

Accordingly, in one aspect, the invention relates to a process for treating pain in mammals, particularly humans, by administering to the mammals, preferably by the oral route and preferably simultaneously, hydrocodone or a pharmaceutically acceptable acid addition salt thereof and ibuprofen or a pharmaceutically acceptable salt thereof.

The present invention particularly provides a pharmaceutical composition comprising a pharmaceutically acceptable carrier and an analgesically effective amount of (a) an analgesic agent selected from the group consisting of hydrocodone and pharmaceutically acceptable acid addition salts thereof; and (b) ibuprofen or a pharmaceutically acceptable salt thereof.

DETAILED DESCRIPTION OF THE INVENTION

The surprising efficacy of the novel compositions of the invention can be demonstrated in various pharmacological procedures. For example in one method used to measure the pain-relieving effects of hydrocodone, ibuprofen and combinations of the two drugs, mice can be given 0.025 ml of 2% carrageenin (in saline) sc into the plantar surface of both hind feet 3.0 hours before treatment. The latency to a distinct response following placement of the mice on a brass hotplate (55° C.) can be measured immediately prior to dosing with the vehicle (0.5% hydroxypropyl-methylcellulose in water) or with drug.

The antinociceptive response is measured by recording the reaction time of the dosed mouse minus the reaction time immediately prior to dosing.

In such a test within the dose range of 1 to 2 mg/kg of hydrocodone and 50 to 100 mg/kg of ibuprofen, the reaction time is greater when using hydrocodone in combination with ibuprofen than that obtained by using either analgesic alone even if the dose is increased.

In a further experiment groups of normal mice can be given hydrocodone, ibuprofen, a mixture containing hydrocodone and ibuprofen or the requisite volume of vehicle per os immediately after measuring the latency to a distinct tail flick (following tail immersion in water at 50° C.).

In such a test within the dose range of 5 to 15 mg/kg of hydrocodone and 100 to 200 mg/kg of ibuprofen, the latency to a distinct tail flick is greater when using hydrocodone and ibuprofen in combination than that obtained by using either analgesic alone even if the dose is increased.

Compositions of the present invention would be expected, in pharmacological tests, to have further advantages. It is well known that non-steroidal antiinflammatory agents such as ibuprofen may be implicated in the causation of gastric erosion and other undesirable side effects. The use of hydrocodone in combination with ibuprofen will reduce the severity of gastric erosion, and provide a significant protective effect. It is also well known that hydrocodone has a narcotic activity, but this is less pronounced with the combination than with hydrocodone alone at an equi-analgesic dose.

The novel compositions of the present invention may be used in alleviating pain in mammals, particularly humans. Thus the invention also provides a method of alleviating pain in mammals which comprises administering to a mammal in need thereof a composition according to the invention. The compositions may be used in alleviating pain, and possibly inflammation, associated with arthritic diseases, e.g., rheumatoid arthritis, Still's disease and osteoarthritis and various types of nonspecific inflammatory or rheumatic conditions. The compositions may also be useful in alleviating pain in other conditions which are not primarily associated with arthritic diseases, for example pain associated with musculo-skeletal injury, soft tissue injury, dental and post-operative pain, e.g., post-partum pain, surgical pain, dysmenorrhea, migrane, tension and sinus headaches and neuralgia, and the like.

Preferably the novel compositions of the invention are in unit dosage form, e.g., as tablets or capsules. In such form the composition is sub-divided in unit doses containing appropriate quantities of the active ingredients (a) and (b). The unit dosage form can be, for example, a capsule or tablet itself or it can be an appropriate number of such compositions in package form. The quantity of the active ingredients in the unit dosage forms may be varied or adjusted according to the particular need of the patient or the condition being treated. For example, one part by weight of hydrocodone or a pharmaceutically acceptable acid addition salt thereof, e.g., the bitartrate salt, may be administered with at least 20 (e.g., 20 to 80, particularly 40) parts by weight ibuprofen or a pharmaceutically acceptable acid addition salt thereof. Unit dosages for alleviation of pain in humans may, for example, contain from about 5 to 10 mg (preferably 6.5 to 8.5 mg, most preferably 7.5 mg) of hydrocodone or a pharmaceutically acceptable salt thereof and 200 to 400 mg (preferably 250 to 350 mg, most preferably 300 mg) of ibuprofenn or a salt thereof.

The compositions of the present invention may be prepared by bringing the active ingredients into association with (e.g., by mixing with) the pharmaceutically acceptable carrier.

Any suitable carrier known in the art can be used to prepare the pharmaceutical composition of the present invention. In such a composition, the carrier is generally a solid or liquid, or a mixture of a solid and a liquid.

Solid form compositions include powders, granules, tablets, capsules (e.g, hard and soft gelatin capsules), suppositories and pessaries. A solid carrier can be, for example, one or more substances which may also act as flavoring agents, lubricants, solubilisers, suspending agents, fillers, compression aids, binders or tablet-disintegrating agents; it can also be an encapsulating material. In powders the carrier is a finely divided solid which is in admixture with the finely divided active ingredient. In tablets the active ingredient is mixed with a carrier having the necessary compression properties in suitable proportions and compacted in the shape and size desired. The powders and tablets preferably contain up to 99%, e.g., from 0.03 to 99%, preferably 1 to 80% of the active ingredient. Suitable solid carriers include, for example, calcium phosphate, magnesium stearate, talc, sugars, lactose, dextrin, starch, gelatin, cellulose, methyl cellulose, sodium carboxymethyl cellulose, polyvinylpyrrolidine, low melting waxes and ion exchange resins.

The term "composition" is intended to include the formulation of the active ingredient with encapsulating material as carrier to give a capsule in which the active ingredient (with or without other carriers) is surrounded by the carrier, which is thus in association with it. Similarly cachets are included.

Liquid form compositions include, for example, solutions, suspensions, emulsions, syrups, elixirs and pressurized compositions. The active ingredient, for example, can be dissolved or suspended in a pharmaceutically acceptable liquid carrier such as water, an organic solvent, a mixture of both or pharmaceutically acceptable oils or fats. The liquid carrier can contain other suitable pharmaceutical additives such as solubilisers, emulsifiers, buffers, preservatives, sweeteners, flavoring agents, suspending agents, thickening agents, colors, viscosity regulators, stabilisers or osmoregulators. Suitable examples of liquid carriers for oral administration include water (particularly containing additives as above, e.g., cellulose derivatives, preferably sodium carboxymethyl cellulose solution), alcohols (including monohydric alcohols (including monohydric alcohols and polyhydric alcohols, e.g., glycerine and non-toxic glycols) and their derivatives, and oils (e.g., fractionated coconut oil and arachis oil).

Preferably the compositions of the present invention are administered orally either in liquid or solid composition form.

DESCRIPTION OF THE PREFERRED EMBODIMENTS

The following Examples illustrate the invention, without limiting the claims.

EXAMPLES 1 TO 4

Tablets of the following compositions are made by mixing batches of the ingredients and compressing to form tablets.

EXAMPLE 1

|  | mg/tablet |
|---|---|
| Hydrocodone bitartrate | 7.5 |
| Ibuprofen | 300.0 |
| Avicel pH 101 (microcrystalline cellulose) | 60.5 |
| Lactose hydrous USP | 20.0 |
| Explotab (sodium starch glycolate USP) | 10.0 |
| Magnesium Stearate USP | 2.0 |
|  | 400.0 |

EXAMPLE 2

|  | mg/tablet |
|---|---|
| Hydrocodone bitartrate | 25.0 |
| Ibuprofen | 300.0 |
| Avicel pH 101 | 247.5 |
| Anhydrous lactose USP | 227.5 |
| Amberlite IRP 88 | 16.0 |
| Magnesium stearate USP | 4.0 |
|  | 800.0 |

EXAMPLE 3

|  | mg/tablet |
|---|---|
| Hydrocodone bitartrate | 5.0 |
| Ibuprofen | 200.0 |
| Avicel pH 101 | 286.0 |
| Anhydrous lactose USP | 100.0 |
| Amberlite IRP 88 | 6.0 |
| Magnesium Stearate USP | 3.0 |
|  | 600.0 |

EXAMPLE 4

|  | mg/tablet |
|---|---|
| Hydrocodone bitartrate | 10.0 |
| Ibuprofen | 400.0 |
| Avicel pH 101 | 186.5 |
| Anhydrous Lactose USP | 100.0 |
| Explotab | 40.0 |
| Talc USP | 10.0 |
| Magnesium stearate USP | 3.5 |
|  | 750.0 |

EXAMPLES 5 to 7

Capsules of the following compositions are made by mixing together batches of the following ingredients and filling hard gelatine capsules with the mixture.

|  | Example 5 mg/capsule | Example 6 mg/capsule | Example 7 mg/capsule |
|---|---|---|---|
| Hydrocodone bitartrate | 7.5 | 5.0 | 10.0 |
| Ibuprofen | 300.0 | 400.0 | 200.0 |
| Lactose hydrous USP | 61.5 | 163.0 | 274.0 |
| Maize starch dried USP | 20.0 | 20.0 | 50.0 |
| Talc USP | 10.0 | 10.0 | 15.0 |
| Magnesium stearate USP | 1.0 | 2.0 | 1.0 |
|  | 400.0 | 600.0 | 550.0 |

While the regimen will be prescribed by the physician or veterinarian depending on the needs of the individual patient, one tablet (or capsule) three to four times per day according to the severity of the pain and the response of the patient will comprise a typical dose schedule.

The foregoing patents and publications are incorporated herein by reference. Many variations in the invention will suggest themselves to those skilled in this art in light of the foregoing detailed description. All such obvious variations are within the full intended scope of the appended claims.

I claim:

1. A process for treating pain in a mammal which comprises administering to the mammal an amount of a pharmaceutical composition effective to provide an analgesic effect, said pharmaceutical composition comprising hydrocodone or a pharmaceutically acceptable acid addition salt thereof and ibuprofen or a pharmaceutically acceptable acid addition salt thereof, the ratio of hydrocodone to ibuprofen being within the range that the administration of a therapeutic amount of said composition to a mammal will provide a greater analgesic effect than the effect obtainable by use of either hydrocodone or a pharmaceutically acceptable acid addition salt thereof or ibuprofen or a pharmaceutically acceptable acid addition salt thereof alone.

2. A pharmaceutical composition which comprises hydrocodone or a pharmaceutically acceptable acid addition salt thereof and ibuprofen or a pharmaceutically acceptable acid addition salt thereof in amounts that are sufficient to provide an analgesic effect, the ratio of hydrocodone to ibuprofen being within the range that the administration of a therapeutic amount of said composition to a mammal will provide a greater analgesic effect than the effect obtainable by use of either hydrocodone or a pharmaceutically acceptable acid addition salt thereof or ibuprofen or a pharmaceutically acceptable acid addition salt thereof alone.

3. A process for treating pain in a mammal which comprises administering to the mammal one part by weight of hydrocodone or a pharmaceutically acceptable acid addition salt thereof and about 20 to 80 parts by weight of ibuprofen or a pharmaceutically acceptable salt thereof.

4. A pharmaceutical composition comprising a pharmaceutically acceptable carrier and an analgesically effective amount of:
    (a) one part by weight of an analgesic agent selected from the group consisting of hydrocodone and pharmaceutically acceptable acid addition salts thereof, and
    (b) about 20 to 80 parts by weight of ibuprofen or a pharmaceutically acceptable salt thereof.

5. A process for treating pain in a mammal which comprises administering to the mammal a dosage unit comprising about 5 to 10 mg. of hydrocodone or a pharmaceutically acceptable acid addition salt thereof and about 200 to 400 mg. of ibuprofen or a pharmaceutically acceptable salt thereof.

6. A pharmaceutical composition in unit dosage form comprising a pharmaceutically acceptable carrier and
    (a) about 5 to 10 mg. of an analgesic agent selected from the group consisting of hydrocodone and pharmaceutically acceptable acid addition salts thereof, and
    (b) about 200 to 400 mg. of ibuprofen or a pharmaceutically acceptable salt thereof.

* * * * *